United States Patent [19]

Rose et al.

[11] Patent Number: 5,089,025
[45] Date of Patent: Feb. 18, 1992

[54] HAIR DYE COMPOSITIONS AND CERTAIN 1,2,3,4-TETRAHYDRONITROQUINOXALINES USEFUL THEREIN

[75] Inventors: David Rose, Hilden; Edgar Lieske; Horst Hoeffkes, both of Duesseldorf, all of Fed. Rep. of Germany

[73] Assignee: Henkel Kommanditgesellschaft auf Aktien, Duesseldorf-Holthausen, Fed. Rep. of Germany

[21] Appl. No.: 640,372

[22] PCT Filed: Jul. 17, 1989

[86] PCT No.: PCT/EP89/00834

§ 371 Date: Jan. 25, 1991

§ 102(e) Date: Jan. 25, 1991

[87] PCT Pub. No.: WO90/01050

PCT Pub. Date: Feb. 8, 1990

[30] Foreign Application Priority Data

Jul. 25, 1988 [DE] Fed. Rep. of Germany ....... 3825212

[51] Int. Cl.$^5$ ............................................. A61K 7/13
[52] U.S. Cl. ........................................... 8/405; 8/406; 8/408; 8/410; 8/415; 8/416; 8/435; 424/70; 564/442; 564/443
[58] Field of Search .................. 8/405, 406, 408, 410, 8/415, 416, 435; 424/70; 564/441, 442, 443

[56] References Cited

U.S. PATENT DOCUMENTS 2,196,739  4/4940  Peterson .............................. 430/470

Primary Examiner—Paul Lieberman
Assistant Examiner—William S. Parks

Attorney, Agent, or Firm—Ernest G. Szoke; Wayne C. Jaeschke; Norvell E. Wisdom, Jr.

[57] ABSTRACT

The invention relates to the use of compounds corresponding to formula (I)

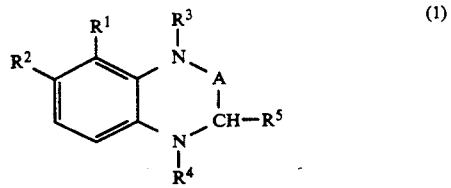

in which one of the substituents $R^1$ or $R^2$ is a nitro group while the other is hydrogen, halogen, an amino group, a mono- or dialkylamino group containing $C_{1-4}$ alkyl groups, a $C_{1-4}$ alkyl or alkoxy group, $R^3$ and $R^4$ independently of one another represent hydrogen or a $C_{1-4}$ alkyl group, A is a $>CHR^6$- or a $>C=O$- group, where $R^6$ is hydrogen or a $C_{1-4}$ alkyl group, and $R^5$ is hydrogen or a $C_{1-4}$ alkyl group, or salts thereof as substantive dyes in hair-dyeing compositions. When the substituent groups in formula I represent one of the combinations I–IV shown in the table below, the compounds are novel and are useful in hair-dyeing compositions.

|      | $R^1$ | $R^2$ | $R^3$ | $R^4$ | $R^5$ | A |
|------|-------|-------|-------|-------|-------|-----|
| I:   | H     | NO$_2$ | H    | CH$_3$ | H    | CH$_2$ |
| II:  | H     | NO$_2$ | CH$_3$ | CH$_3$ | H  | CH$_2$ |
| III: | NH$_2$ | NO$_2$ | H   | H     | H    | CH$_2$ |
| IV:  | H     | NO$_2$ | H    | H     | CH$_3$ | CH$_2$. |

20 Claims, No Drawings

HAIR DYE COMPOSITIONS AND CERTAIN 1,2,3,4-TETRAHYDRONITROQUINOXALINES USEFUL THEREIN

BACKGROUND OF THE INVENTION

1. Field of the Invention

This invention relates to hair-dyeing compositions containing substantive hair dyes and to certain novel 1,2,3,4-tetrahydronitroquinoxalines useful therein.

2. Statement of Related Art

In addition to oxidation dyes, which are formed by the oxidative coupling of one or more primary intermediate components with one another or with one or more coupler components, substantive hair dyes play a prominent part in the dyeing of hair. Substantive dyes have the advantage that they can be used without the addition of oxidizing agents. The substantive dyes used are predominantly compounds belonging to the group of nitrobenzene derivatives. They are used either on their own or in combination with other substantive dyes, such as anthraquinone dyes, indophenols, triphenylmethane dyes, cationic azo dyes, or with oxidation dyes.

Hair-dyeing compositions of the type in question normally contain such substantive hair dyes in a cosmetic carrier. The cosmetic carriers used for the substantive hair dyes and for the oxidation dye intermediates, if any, additionally present to obtain certain color tones include creams, emulsions, gels, shampoos, foam aerosols, or other compositions suitable for application to the hair.

Good hair-dyeing compositions have to form the required colors with sufficient intensity. They must be readily absorbed by human hair without excessively staining the scalp. The coloration produced with them must show high stability to light, heat, perspiration, shampoos, and the chemicals used in the permanent waving of hair. Finally, they should be safe to use from the toxicological and dermatological viewpoint.

In addition, substantive dyes are required to show high compatibility with other dyes, for example with oxidation dye intermediates and with the components normally used in oxidation hair-dyeing compositions because substantive dyes and oxidation dyes are often combined with one another for color tone modification. Accordingly, high stability to reducing agents and oxidizing agents is necessary.

Among the substantive nitrobenzene derivatives, the nitroanilines and derivatives thereof play an important part because some of these dyes produce intensive, light-stable hair colors. However, the known substantive nitroaniline dyes have disadvantages in that, on the one hand, they show only limited solubility in water, which leads to problems during formulation of the hair-dyeing compositions, and on the other hand are not sufficiently fast to washing, i.e., the dye finishes fade considerably after repeated washing of the hair. In addition, it is difficult when using substantive dyes to obtain certain fashionable tints, particularly red tints. Hitherto, 2-nitro-p-phenylenediamine and amino-substituted derivatives thereof have generally been used for this purpose. However, most of these compounds show inadequate solubility or dispersibility in water. This often leads to uneven hair colors. In addition, there is a danger, particularly with dyeing compositions containing high concentrations of dyes to obtain certain color tones, but also with compositions containing only sparingly solubilizing carrier components, of the colors obtained being weaker than expected because the dyes crystallize out and remain in the dye bath instead of being absorbed onto the hair.

DESCRIPTION OF THE INVENTION

It has surprisingly been found that certain 1,2,3,4-tetrahydronitroquinoxalines do not have the disadvantages mentioned and, accordingly, satisfy the requirements of substantive hair dyes to a high degree.

Accordingly, the present invention relates to hair-dyeing compositions containing substantive dyes which are characterized in that they contain one or more compounds corresponding to formula (I):

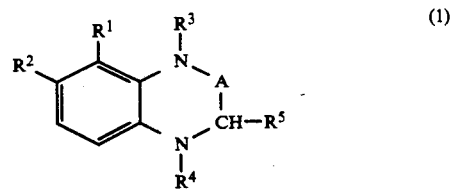

in which one of the substituents $R^1$ or $R^2$ is a nitro group while the other is hydrogen, halogen, an amino group, a mono- or dialkylamino group containing $C_{1-4}$ alkyl groups, a $C_{1-4}$ alkyl or alkoxy group; $R^3$ and $R^4$ independently of one another represent hydrogen or a $C_{1-4}$ alkyl group; A is a $>CHR^6$ or a $>C=O$ group, where $R^6$ is hydrogen or a $C_{1-4}$ alkyl group; and $R^5$ is hydrogen or a $C_{1-4}$ alkyl group, or salts thereof as the substantive dyes.

Particularly suitable dyes are 1,2,3,4-tetrahydro-5-nitroquinoxaline and 1,2,3,4-tetrahydro-6-nitroquinoxaline.

The dyes according to the invention may generally be obtained from the correspondingly substituted quinoxalines by standard synthesis methods. Thus, the preparation of 1,2,3,4-tetrahydro-5-nitroquinoxaline and 1,2,3,4-tetrahydro-6-nitroquinoxaline by reaction of the corresponding quinoxalines with sodium borohydride in methanolic solution is described in *J. Het. Chem.* 10, 213 (1973). However, compounds corresponding to formula (I) may also be obtained by other methods. Thus, 1,2,3,4-tetrahydro-7-nitro-2-oxoquinoxaline may be obtained in accordance with *J. Chem. Soc.* (1961), 5283 by reaction of N-(2,4-dinitrophenyl)glycine with a mixture of sodium hydrogen carbonate and sodium sulfide in methanolic solution.

However, there is no reference in any of the above-cited publications to the suitability of these compounds for the dyeing of hair.

Compounds corresponding to formula (I) in claim 1 characterized by the following substituent combinations (I) to (IV):

|     | $R^1$ | $R^2$ | $R^3$ | $R^4$ | $R^5$ | A |
| --- | --- | --- | --- | --- | --- | --- |
| I:  | H   | NO$_2$ | H   | CH$_3$ | H   | CH$_2$ |
| II: | H   | NO$_2$ | CH$_3$ | CH$_3$ | H   | CH$_2$ |
| III:| NH$_2$ | NO$_2$ | H   | H   | H   | CH$_2$ |
| IV: | H   | NO$_2$ | H   | H   | CH$_3$ | CH$_2$ | are new and are therefore a further subject of the present invention.

In principle, these compounds may also be obtained from the correspondingly substituted quinoxalines; synthesis procedures are described in the Examples.

The dyes corresponding to general formula (I) produce yellow to red-orange color tones of high intensity and high fastness to light and washing on the hair. In addition, they show better solubility in aqueous alkaline media than known nitroaniline dyes. The compounds mentioned are dermatologically and toxicologically safe and are therefore particularly suitable for use in hair-dyeing compositions.

The dyes according to the invention may be used both as such and in the form of their water-soluble salts. In this connection, salts are regarded as water-soluble when they dissolve in water or aqueous mixtures in a quantity sufficient for dyeing hair.

In the context of the invention, the water-soluble salts are primarily understood to be the salts of strong bases, such as for example the alkali metal salts, for example the sodium or potassium salt, or ammonium salts and alkanolammonium salts containing from 2 to 4 carbon atoms in the alkanol group, such as for example the monoethanolammonium salt, the triethanolammonium salt, or the isopropanolammonium salt. The hair-dyeing compositions according to the invention may contain the substantive compounds corresponding to general formula I either on their own or in combination with known substantive dyes, for example with other nitrobenzene derivatives, anthraquinone dyes, triphenylmethane or azo dyes. In addition, the substantive dyes of general formula I, by virtue of their high resistance to reducing agents and oxidizing agents, are also eminently suitable for combination with oxidation dye intermediates, i.e. for modifying the colors of oxidation hair dyes. Oxidation hair dyes contain as dye intermediates primary intermediate components which form the oxidation dyes by oxidative coupling with one another or with suitable coupler components. The primary intermediate components used are, for example, primary aromatic amines containing another free or substituted hydroxy or amino group in the para or ortho position, diaminopyridine derivatives, heterocyclic hydrazones, 4-aminopyrazolone derivatives, and 2,4,5,6-tetraaminopyrimidine and derivatives thereof. The coupler components used are m-phenylenediamine derivatives, naphthols, resorcinol and resorcinol derivatives, pyrazolones and m-aminophenols.

To produce the hair-dyeing compositions according to the invention, the substantive hair dyes and the oxidation dye intermediates, if any, are incorporated in a suitable cosmetic carrier, for example in creams, emulsions, gels, or even surfactant-containing foaming solutions, for example in shampoos, foam aerosols, or other compositions which are suitable for application to the hair.

Typical ingredients of cosmetic compositions of this type are, for example, wetting agents and emulsifiers, such as anionic, nonionic or ampholytic surfactants, for example fatty alcohol sulfates, alkane sulfonates, $\alpha$-olefin sulfonates, fatty alcohol polyglycolether sulfates, ethylene oxide adducts with fatty alcohols, fatty acids and alkylphenols, sorbitan fatty acid esters and fatty acid partial glycerides, fatty acid alkanolamides; thickeners such as, for example, methyl or hydroxyethyl cellulose, starch, fatty alcohols, paraffin oils, fatty acids; also perfume oils and hair-care additives such as, for example, water-soluble cationic polymers, protein derivatives, pantothenic acid and cholesterol. The constituents of the cosmetic carriers are used in the usual quantities for producing the hair-dyeing compositions according to the invention; for example, emulsifiers are used in concentrations of from 0.5 to 30% by weight and thickeners in concentrations of from 0.1 to 25% by weight, based on the composition as a whole.

The substantive dyes corresponding to general formula I are used in the hair-dyeing compositions according to the invention in a quantity of from 0.01 to 5.0% by weight and preferably in a quantity of from 0.1 to 2% by weight, based on the hair-dyeing composition as a whole. In addition, known oxidation hair dye intermediates (primary intermediates and couplers) may be present in a quantity of from 0.01 to 5% by weight and preferably in a quantity of from 1 to 3% by weight.

Where the hair-dyeing composition according to the invention contains oxidation dye intermediates, it is advisable to add a small quantity of a reducing agent, for example from 0.5 to 2.0% by weight of sodium sulfite, to stabilize the oxidation dye intermediates. In this case, an oxidizing agent is added to the hair-dyeing composition before use in order to initiate oxidative development of the oxidation dye intermediates. Suitable oxidizing agents are, in particular, hydrogen peroxide or adducts thereof with urea, melamine, or sodium borate and also mixtures of these hydrogen peroxide adducts with potassium peroxydisulfate.

The hair dyes according to the invention may be used in a mildly acidic, neutral or alkaline medium, irrespective of the type of cosmetic composition used, for example a cream, gel, or shampoo. The hair dyes are preferably used in the pH range from 6 to 10. They may be used at temperatures of from 15° to 40° C. After a contact time of around 30 minutes, the hair-dyeing composition is removed by rinsing from the hair to be dyed. The hair is then washed with a mild shampoo and dried. Washing with a shampoo is unnecessary when a carrier of high surfactant content, for example a dye shampoo, is used.

Hair colors of high intensity and good fastness properties, particularly to washing, and high stability to bleeding and changes in color during shampooing may be obtained with the hair-dyeing compositions according to the invention. The following Examples are intended to illustrate the invention without limiting it in any way.

EXAMPLES

Synthesis Examples

1.) 1,2,3,4-tetrahydro-2-methyl-6-nitroquinoxaline 1 g 2-methyl-6-nitroquinoxaline synthesized by the method described in *Coll. Czech. Chem. Comm.* 30, 3106 (1965) from 4-nitro-1,2-diaminobenzene by reaction with methyl glyoxal was dissolved in 30 ml acetic acid. Sodium borohydride was added to this solution in small portions at +5° C. until the starting compound could no longer be detected in the solution by thin-layer chromatography. The solution was then diluted with 200 ml water and extracted twice with chloroform. The organic phase was washed with water and dried. After concentration to dryness, the residue was dissolved in acetone and precipitated with hydrochloric acid. The yield amounted to 0.6 g (58% of the theoretical). The melting point of the 1,2,3,4-tetrahydro-2-methyl-6-nitroquinoxaline thus obtained was 178° C.

2.) 1,2,3,4-tetrahydro-5-amino-6-nitroquinoxaline

5-Amino-6-nitroquinoxaline was synthesized by reaction of 6-nitroquinoxaline with hydroxylamine in an alkaline medium in accordance with *J. Chem. Soc., Perkin I,* 1975, 1229. The product was reacted With sodium borohydride as in Example 1). The 1,2,3,4-tetrahydro-5- amino-6-nitroquinoxaline obtained in the form of brown crystals in a yield of 11.5% of the theoretical had a melting point of 213° C.

3.) N,N'-dimethyl-1,2,3,4-tetrahydro-6-nitroquinoxaline 1.52 g (0.024 mole) sodium cyanoborohydride was added at 25° C., to a mixture of 1.08 g (0.006 mole) of the 1,2,3,4-tetrahydro-6-nitroquinoxaline obtained in accordance with *J. Het. Chem.* 10, 213 (1973) and 1.5 g (0.005 mole) paraformaldehyde in 300 ml acetic acid. The solution was then left standing for 24 hours at room temperature. The solution was then poured into 60 ml 25% aqueous NaOH solution. The mixture obtained was then extracted three times with methylene chloride. After drying and concentration, N,N'-dimethyl-1,2,3,4-tetrahydro-6-nitroquinoxaline was obtained in a yield of 0.35 g (35% of the theoretical). The melting point of the product was 70° C.

4 ) 1-(N-methyl)-1,2,3,4-tetrahydro-6-nitroquinoxaline

Step 1:

A mixture of 21.75 g (0.14 mole) 2-fluoro-5-nitroaniline, 56 g (0.74 mole) 2-methylaminoethanol and 1 g copper (II) oxide was heated for 1.5 hours to 120° C. After cooling, the catalyst was filtered off and the solution was poured onto ice water. The precipitate formed was filtered off under suction and dried in vacuo at +70° C. The yield of 1-(N-methyl-N-B-hydroxyethyl)-2-amino-4-nitrobenzene amounted to 25.5 g (96% of the theoretical). The melting point of the product was 111°–113° C.

Step 2:

5 g of the product obtained in step 1 was introduced into 22 ml phosphorus oxytrichloride over a period of 15 minutes at room temperature. The mixture was then heated in a water bath for 1 hour. After the excess phosphorus oxytrichloride had been distilled off, 50 ml distilled water was added to the residue which was then extracted with diethyl ether. The orange-colored oil obtained by concentration of the ethereal phase was refluxed for 16 hours with ethanol and concentrated in vacuo to dryness. The residue obtained was dissolved in water, and potassium carbonate solution was added to the resulting solution until the mixture showed an alkaline reaction. The precipitate formed was filtered off under suction and dried in vacuo at 60° C. Orange-red crystals of 1-(N-methyl)-1,2,3,4-tetrahydro-6-nitroquinoxaline were obtained. The UV spectrum of these crystals recorded with ethanol as the solvent showed maxima at 441 nm, 350 nm, and 290 nm.

HAIR-DYEING TESTS

Hair-dyeing creams were prepared from the following constituents:

$C_{12-18}$ fatty alcohol: 10 g
$C_{12-14}$ fatty alcohol+2 EO sulfate, Na salt (28%): 25 g
Water: 60 g
Substantive dye: 1 g
Ammonium sulfate: 1 g
Concentrated ammonia solution: to pH=9.5
Water: ad 100 g The constituents were mixed together in the above order. After addition of the substantive dyes, the emulsion was first adjusted to pH 9.5 with concentrated ammonia solution and then made up with water to 100 g.

The dye cream was applied to ca. 5 cm long strands of standardized, 90% gray, but not specially pretreated human hair and left thereon for 30 minutes at 27° C. After dyeing, the hair was rinsed, washed with a standard shampoo and then dried.

The results of the dyeing tests are shown in Table I.

TABLE I

| Substantive dye | Color of the dyed hair |
| --- | --- |
| 1,2,3,4-Tetrahydro-5-nitroquinoxaline | Gray-red |
| 1,2,3,4-Tetrahydro-6-nitroquinoxaline | Copper |
| 1,2,3,4-Tetrahydro-7-nitro-2-oxoquinoxaline | Olive-brown |
| 1,2,3,4-Tetrahydro-2-methyl-6-nitro-quinoxaline | Red-gold |
| 1,2,3,4-Tetrahydro-5-amino-6-nitro-quinoxaline | Yellow |
| N,N'-Dimethyl-1,2,3,4-tetrahydro-6-nitro-quinoxaline | Red-orange |
| 1-(N-methyl)-1,2,3,4-tetrahydro-6-nitro-quinoxaline | Red-brown |

What is claimed is:

1. Hair-dyeing compositions comprising suitable cosmetic carriers and substantive dyes, wherein the improvement comprises the presence in the compositions of one or more compounds, or water-soluble salts of compounds, corresponding to formula (I):

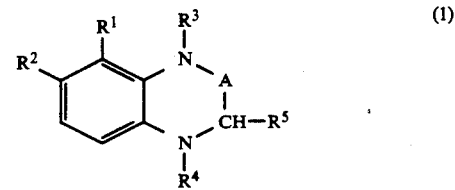

in which one of the substituents $R^1$ or $R^2$ is a nitro group while the other is selected from the group consisting of hydrogen, halogen, amino, a mono- and di-alkylamino containing $C_{1-4}$ alkyl groups, $C_{1-4}$ alkyl and alkoxy group; $R^3$ and $R^4$ independently of one another represent hydrogen or a $C_{1-4}$ alkyl group; A is a >CHR$^6$ or a >C=O group, where $R^6$ is hydrogen or a $C_{1-4}$ alkyl group; and $R^5$ is hydrogen or a $C_{1-4}$ alkyl group, as substantive dyes.

2. Hair-dyeing compositions as claimed in claim 1, comprising 1,2,3,4-tetrahydro-5-nitroquinoxaline or 1,2,3,4-tetrahydro-6-nitroquinoxaline as substantive dyes.

3. Hair-dyeing compositions as claimed in claim 2, wherein the substantive dyes corresponding to formula (I) are present in a quantity of from 0.01 to 5% by weight, based on the hair-dyeing composition as a whole.

4. Hair-dyeing compositions as claimed in claim 3, wherein other substantive dyes or oxidation dye intermediates are present in addition to the compounds of formula (I).

5. Hair-dyeing compositions as claimed in claim 4, wherein the cosmetic carrier is in the form of a cream, an emulsion, a gel, a shampoo, or a foam aerosol.

6. A composition of matter corresponding to formula (I):

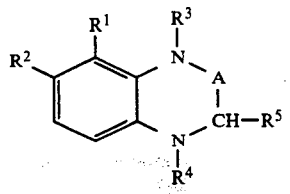

wherein $R^1$, $R^2$, $R^3$, $R^4$, $R^5$, and A have one of the combinations (I) to (IV) of meanings given in the following table:

| | $R^1$ | $R^2$ | $R^3$ | $R^4$ | $R^5$ | A |
|---|---|---|---|---|---|---|
| I: | H | $NO_2$ | H | $CH_3$ | H | $CH_2$ |
| II: | H | $NO_2$ | $CH_3$ | $CH_3$ | H | $CH_2$ |
| III: | $NH_2$ | $NO_2$ | H | H | H | $CH_2$ |
| IV: | H | $NO_2$ | H | H | $CH_3$ | $CH_2$. |

7. Hair-dyeing compositions as claimed in claim 1, wherein the substantive dyes corresponding to formula (I) are present in a quantity of from 0.01 to 5% by weight, based on the hair-dyeing composition as a whole.

8. Hair-dyeing compositions as claimed in claim 7, wherein the substantive dyes corresponding to formula (I) are present in a quantity of from 0.1 to 2% by weight, based on the hair-dyeing composition as a whole.

9. Hair-dyeing compositions as claimed in claim 3, wherein the substantive dyes corresponding to formula (I) are present in a quantity of from 0.1 to 2% by weight, based on the hair-dyeing composition as a whole.

10. Hair-dyeing compositions as claimed in claim 9, wherein other substantive dyes or oxidation dye intermediates are present in addition to the compounds of formula (I).

11. Hair-dyeing compositions as claimed in claim 8, wherein other substantive dyes of oxidation dye intermediates are present in addition to the compounds of formula (I).

12. Hair-dyeing compositions as claimed in claim 7, wherein other substantive dyes or oxidation dye intermediates are present in addition to the compounds of formula (I).

13. Hair-dyeing compositions as claimed in claim 5, wherein other substantive dyes or oxidation dye intermediates are present in addition to the compounds of formula (I).

14. Hair-dyeing compositions as claimed in claim 2, wherein other substantive dyes or oxidation dye intermediates are present in addition to the compounds of formula (I).

15. Hair-dyeing compositions as claimed in claim 1, wherein other substantive dyes or oxidation dye intermediates are present in addition to the compounds of formula (I).

16. Hair-dyeing compositions as claimed in claim 15, wherein the cosmetic carrier is in the form of a cream, an emulsion, a gel, a shampoo, or a foam aerosol.

17. Hair-dyeing compositions as claimed in claim 14, wherein the cosmetic carrier is in the form of a cream, an emulsion, a gel, a shampoo, or a foam aerosol.

18. Hair-dyeing compositions as claimed in claim 3, wherein the cosmetic carrier is in the form of a cream, an emulsion, a gel, a shampoo, or a foam aerosol.

19. Hair-dyeing compositions as claimed in claim 2, wherein the cosmetic carrier is in the form of a cream, an emulsion, a gel, a shampoo, or a foam aerosol.

20. Hair-dyeing compositions as claimed in claim 1, wherein the cosmetic carrier is in the form of a cream, an emulsion, a gel, a shampoo, or a foam aerosol.

* * * * *